United States Patent
Jang et al.

(10) Patent No.: US 11,969,234 B2
(45) Date of Patent: Apr. 30, 2024

(54) APPARATUS AND METHOD FOR ESTIMATING BIO-INFORMATION

(71) Applicant: SAMSUNG ELECTRONICS CO., LTD., Suwon-si (KR)

(72) Inventors: Dae Geun Jang, Yongin-si (KR); Ui Kun Kwon, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 411 days.

(21) Appl. No.: 16/880,458

(22) Filed: May 21, 2020

(65) Prior Publication Data

US 2021/0169356 A1 Jun. 10, 2021

(30) Foreign Application Priority Data

Dec. 10, 2019 (KR) ........................ 10-2019-0163401

(51) Int. Cl.
*A61B 5/022* (2006.01)
*A61B 5/00* (2006.01)
(Continued)

(52) U.S. Cl.
CPC ...... *A61B 5/02225* (2013.01); *A61B 5/02007* (2013.01); *A61B 5/02116* (2013.01); (Continued)

(58) Field of Classification Search
CPC ............ A61B 5/02225; A61B 5/02007; A61B 5/02116; A61B 5/02233; A61B 5/681; A61B 5/725; A61B 5/6843; A61B 5/02416; A61B 5/02108; A61B 5/0295; A61B 5/7275; G16H 50/30
See application file for complete search history.

(56) References Cited

U.S. PATENT DOCUMENTS 5,784,304 A * 7/1998 Koike ................ H03H 21/0012
708/322
6,358,213 B1 3/2002 Friedman et al.
(Continued)

FOREIGN PATENT DOCUMENTS

JP 2016-220886 A 12/2016
KR 10-2010-0120972 A 11/2010
(Continued)

OTHER PUBLICATIONS

A Developed Algorithm for Oscillometric Blood Pressure Measurement published 2013, IEEE. (Year: 2013).*
(Continued)

*Primary Examiner* — Shahdeep Mohammed
*Assistant Examiner* — Fikirte (Fiki) T Ashine
(74) *Attorney, Agent, or Firm* — Sughrue Mion, PLLC

(57) ABSTRACT

An apparatus for estimating bio-information includes a bio-signal obtainer configured to obtain a bio-signal from an object; and a processor configured to: obtain function values by applying a predetermined function to sections of the bio-signal, corresponding to respective windows of a predetermined size, while sliding a window on a time axis of the bio-signal, obtain an oscillometric waveform envelope based on the obtained function values, and estimate bio-information of the object based on the oscillometric waveform envelope.

11 Claims, 12 Drawing Sheets

(51) Int. Cl.
*A61B 5/02* (2006.01)
*A61B 5/021* (2006.01)
*G16H 50/30* (2018.01)

(52) U.S. Cl.
CPC .......... *A61B 5/02233* (2013.01); *A61B 5/681* (2013.01); *A61B 5/725* (2013.01); *G16H 50/30* (2018.01)

(56) References Cited

U.S. PATENT DOCUMENTS

| | | |
|---|---|---|
| 6,808,496 B2 | 10/2004 | Oka et al. |
| 8,747,327 B2 | 6/2014 | Kim et al. |
| 10,191,307 B2 | 1/2019 | Fujita et al. |
| 2003/0097074 A1 | 5/2003 | Oka et al. |
| 2012/0283583 A1 | 11/2012 | Batkin et al. |
| 2013/0079647 A1 | 3/2013 | McGonigle et al. |
| 2015/0257669 A1 | 9/2015 | Ben-David et al. |
| 2018/0256045 A1 | 9/2018 | Liu et al. |

FOREIGN PATENT DOCUMENTS

| | | |
|---|---|---|
| KR | 10-2011-0037202 A | 4/2011 |
| WO | 2016/152128 A1 | 9/2016 |

OTHER PUBLICATIONS

"A Developed Algorithm for Oscillometric Blood Pressure Measurement", published on 2013, IEEE, Min Chen et al., (Year: 2013).*

"Improved Estimation of the Amplitude Envelope of Time-Domain Signals Using True Envelope Cepstral Smoothing" published on 2011, IEEE. Caetano et al. (Year: 2011).*

Min Chen et al., "A Developed Algorithm for Oscillometric Blood Pressure Measurement", published on 2013, IEEE, (Year: 2013).*

Caetano et al., "Improved Estimation of the Amplitude Envelope of Time-Domain Signals Using True Envelope Cepstral Smoothing" published on 2011, IEEE. (Year: 2011).*

Min Chen et al., "A Developed Algorithm for Oscillometric Blood Pressure Measurement" (Year: 2013).*

Caetano et al., "Improved Estimation of the Amplitude Envelope of Time-Domain Signals Using True Envelope Cepstral Smoothing" (Year: 2011).*

Branko G. Celler et al., "Novel methods of testing and calibration of oscillometric blood pressure monitors", PLOS ONE, Aug. 6, 2018, pp. 1-14.

Wendy Van Moer et al., "Linearizing Oscillometric Blood-Pressure Measurements: (Non)Sense?", IEEE Transactions on Instrumentation and Measurement, vol. 60, Issue 4, IEEE, Apr. 2011, pp. 1-2.

* cited by examiner

APPARATUS AND METHOD FOR ESTIMATING BIO-INFORMATION

CROSS-REFERENCE TO RELATED APPLICATION(S)

This application claims priority from Korean Patent Application No. 10-2019-0163401, filed on Dec. 10, 2019, in the Korean Intellectual Property Office, the entire disclosure of which is herein incorporated by reference for all purposes.

BACKGROUND

1. Field

Example embodiments relate to estimating bio-information by analyzing a waveform of a bio-signal, and more particularly, to obtaining an oscillometric waveform envelope of a bio-signal.

2. Description of the Related Art

Recently, with the aging population, soaring medical costs, and a lack of medical personnel for specialized medical services, research is being actively conducted on information technology (IT)-medical convergence technologies, in which IT technology and medical technology are combined. Particularly, monitoring of the health condition of the human body is not limited to places such as hospitals, but is expanding to mobile healthcare fields that may monitor a user's health state anywhere and anytime in daily life at home or office. Typical examples of bio-signals, which indicate the health condition of individuals, include an electrocardiography (ECG) signal, a photoplethysmogram (PPG) signal, an electromyography (EMG) signal, and the like, and various bio-signal sensors are being developed to measure these signals in daily life. Particularly, a PPG sensor may estimate blood pressure of a human body by analyzing the shape of pulse waves which reflect a cardiovascular status and the like.

SUMMARY

One or more example embodiments provide an apparatus and a method for estimating bio-information with high accuracy by stably obtaining an oscillometric waveform envelope even in a high signal-to-noise environment.

According to an aspect of an example embodiment, there is provided an apparatus for estimating bio-information, the apparatus including: a bio-signal obtainer configured to obtain a bio-signal from an object; and a processor configured to: obtain function values by applying a predetermined function to sections of the bio-signal, corresponding to respective windows of a predetermined size, while sliding a window on a time axis of the bio-signal, obtain an oscillometric waveform envelope based on the obtained function values, and estimate bio-information of the object based on the oscillometric waveform envelope.

The bio-signal may include at least one of photoplethysmogram (PPG), impedance plethysmogram (IPG), pressure wave, and video plethysmogram (VPG).

The processor may be further configured to slide the window by an interval of the predetermined size or by a reference time interval which is smaller than the predetermined size.

The processor may be further configured to equalize the oscillometric waveform envelope by applying a preprocessing algorithm to the obtained oscillometric waveform envelope.

The preprocessing algorithm may include at least one of Savitzky-Golay filtering, polynomial fitting, and Gaussian fitting.

The predetermined size may be set based on at least one of a user input, a user characteristic, an external environment characteristic, and a type of bio-information to be estimated.

The predetermined function may include a function for obtaining a root mean square (RMS) of amplitude values of a section of the bio-signal corresponding to a respective window.

The predetermined function may include a function for obtaining a sum of absolute (ABS) of amplitude values of a section of the bio-signal corresponding to a respective window.

The processor may be further configured to: obtain a first ABS value of amplitude values greater than a reference amplitude value and a second ABS value of amplitudes values lower than the reference amplitude value, among the amplitude values of the section of the bio-signal; and obtain an ABS value of the section of the bio-signal based on a combination of the first ABS value and the second ABS value.

By applying a preprocessing function to the first ABS value and the second ABS value, the processor may be further configured to combine the preprocessed first ABS value and the preprocessed second ABS value.

By applying a combination function including at least one of a multiplication and an addition, the processor may be further configured to combine the first ABS value and the second ABS value.

The estimated bio-information may include at least one of blood pressure, vascular age, arterial stiffness, aortic pressure waveform, vascular compliance, stress index, and fatigue level.

The apparatus may further include a pressure sensor configured to obtain a pressure applied by the object while the bio-signal is obtained, wherein the processor is further configured to estimate the bio-information based on the oscillometric waveform envelope and the obtained pressure.

According to an aspect of an example embodiment, there is provided a method of estimating bio-information, the method including: obtaining a bio-signal from an object; obtaining function values by applying a predetermined function to sections of the bio-signal, corresponding to respective windows of a predetermined size, while sliding a window on a time axis of the bio-signal; obtaining an oscillometric waveform envelope based on the obtained function values; and estimating the bio-information based on the oscillometric waveform envelope.

The obtaining the oscillometric waveform envelope may include obtaining the oscillometric waveform envelope by applying a preprocessing algorithm based on each of the obtained function values.

The predetermined function may include a function for obtaining a root mean square (RMS) of amplitude values of a section of the bio-signal corresponding to a respective window.

The predetermined function may include a function for obtaining a sum of absolute (ABS) of amplitude values of a section of the bio-signal corresponding to a respective window.

The obtaining the function values may include: obtaining a first ABS value of amplitude values greater than a reference amplitude value and a second ABS value of amplitude values lower than the reference amplitude value, among the amplitude values of the section of the bio-signal; and obtaining an ABS value of the section of the bio-signal based on a combination of the first ABS value and the second ABS value.

The method may further include obtaining a pressure applied by the object while the bio-signal is obtained from the object, wherein the estimating includes estimating the bio-information based on the oscillometric waveform envelope and the obtained pressure.

The method may further include equalizing the oscillometric waveform envelope by applying a preprocessing algorithm to the oscillometric waveform envelope, wherein the estimating comprises estimating the bio-information based on the equalized oscillometric waveform envelope.

BRIEF DESCRIPTION OF THE DRAWINGS

The above and/or other aspects will be more apparent from the following description of example embodiments taken in conjunction with the accompanying drawings, in which.

DETAILED DESCRIPTION

Figure 1:
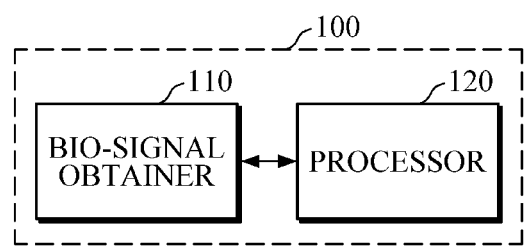
FIG. 1 is a block diagram illustrating an apparatus for estimating bio-information according to an example embodiment.

Details of example embodiments are included in the following detailed description and drawings. Advantages and features of the disclosure, and a method of achieving the same will be more clearly understood from the following example embodiments described in detail with reference to the accompanying drawings. Throughout the drawings and the detailed description, unless otherwise described, the same drawing reference numerals will be understood to refer to the same elements, features, and structures. The relative size and depiction of these elements may be exaggerated for clarity, illustration, and convenience.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module,' etc., should be understood as a unit that performs at least one function or operation and that may be embodied as hardware, software, or a combination thereof.

As used herein, the term "and/or" includes any and all combinations of one or more of the associated listed items. Expressions such as "at least one of" when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

In the present specification, it should be understood that the terms, such as 'including' or 'having,' etc., are intended to indicate the existence of the features, numbers, steps, a Lions, components, parts, or combinations thereof disclosed in the specification, and are not intended to preclude the possibility that one or more other features, numbers, steps, actions, components, parts, or combinations thereof may exist or may be added.

Hereinafter, example embodiments of an apparatus and method for estimating bio-information will be described in detail with reference to the accompanying drawings. The apparatus for estimating bio-information may be mounted in a portable device, such as a smart device, a wearable device, and the like, as well as medical equipment in medical institutions, a cuff manometer, and the like. However, the apparatus for estimating bio-information is not limited thereto.

FIG. 1 is a block diagram illustrating an apparatus 100 for estimating bio-information according to an example embodiment.

Referring to FIG. 1, the apparatus 100 for estimating bio-information includes a bio-signal obtainer 110 and a processor 120.

The bio-signal obtainer 110 may obtain a bio-signal from an object. The bio-signal may include photoplethysmogram (PPG), impedance plethysmogram (IPG), pressure wave, video plethysmogram (VPG), and the like. The bio-signal obtainer 110 may include various types of sensors, e.g., an optics-based sensor, an impedance-based sensor, a pressure-based sensor, etc., depending on the types of bio-signals to be obtained. However, the bio-signal obtainer 110 is not limited thereto, and may also obtain a bio-signal from an external apparatus for measuring a bio-signal, e.g., a cuff manometer, by using a communication interface that will be described below with reference to FIG. 2.

Hereinafter, an example embodiment will be described in detail, in which the bio-signal obtainer 110 includes an optics-based sensor (hereinafter referred to as a "pulse wave sensor") for measuring a PPG signal (hereinafter referred to as a "pulse wave signal"), and obtains the pulse wave signal by using the pulse wave sensor and an oscillometric waveform envelope from the pulse wave signal. However, this is merely for convenience of explanation, and it will be evident to those skilled in the art that the example embodiments which will be described below are not limited to the PPG signal.

The pulse wave sensor includes a light source which emits light onto an object and a detector which detects light scattered or reflected from the object. The light source may include a light emitting diode (LED), a laser diode, a phosphor, and the like. Further, the detector may include a photo diode, an image sensor, and the like, but is not limited thereto. The light source and/or the detector may be formed as an array of two or more light sources and/or detectors, and each of the light sources may emit light of different wavelengths.

The processor 120 may be electrically connected to the pulse wave sensor of the bio-signal obtainer 110, and may control the pulse wave sensor to obtain a pulse wave signal from the object. The object may be skin tissue of a human body and may be, for example, a body part such as the back of the hand, the wrist, fingers, and the like, at which veins or capillaries are located. However, the object is not limited thereto, and may be a body part at which arteries, such as the radial artery, are located.

Upon receiving the pulse wave signal of the object, the processor 120 may remove noise from the pulse wave signal by performing, for example, band-pass filtering between 0.4 Hz to 10 Hz, and the like. Alternatively, the processor 120 may correct the pulse wave signal by reconstructing the pulse wave signal using Fast Fourier Transform (FFT), but is not limited thereto.

The processor 120 may obtain an oscillometric waveform envelope from the pulse wave signal of the object. As will be described below in detail with reference to FIGS. 3A, 3B, and 3C, the processor 120 may apply a predetermined function for a plurality of time intervals of the pulse wave signal, and may obtain the oscillometric waveform envelope based on a calculation result of the predetermined function.

Further, upon obtaining the oscillometric waveform envelope, the processor 120 may detect characteristic points for estimating bio-information by using the oscillometric waveform envelope, and may estimate bio-information by using the detected characteristic points. In this case, bio-information may include blood pressure, vascular compliance, cardiac output, total peripheral resistance, vascular age, and the like, but is not limited thereto.

For example, the processor 120 may detect a maximum peak of the oscillometric waveform envelope as a characteristic point, and may estimate blood pressure based on the detected maximum peak. For example, in addition to the maximum peak, the processor 120 may detect, as additional characteristic points, waveform components related to propagation waves and/or reflection waves of the pulse waves, a total or partial area of the pulse wave signal, and the like, and may obtain features for estimating blood pressure by using one or a combination of two or more of the detected characteristic points. Further, the processor 120 may estimate blood pressure based on the obtained features by applying a pre-defined bio-information estimation model.

In another example, the processor 120 may obtain time points, located before and after the maximum peak and corresponding to amplitude values having a predetermined ratio (e.g., 0.5 to 0.7) to an amplitude value of the maximum peak, as features for diastolic blood pressure and systolic blood pressure respectively, and may estimate diastolic blood pressure and systolic blood pressure respectively from the features for diastolic blood pressure and systolic blood pressure by applying the bio-information estimation model.

In yet another example, the processor 120 may obtain contact pressure when the object, which is in contact with the pulse wave sensor, gradually increases pressure, and may obtain diastolic blood pressure and systolic blood pressure by further using the obtained contact pressure. In this case, the amplitude of the pulse wave signal is changed with a change in pressure applied by the object to the pulse wave sensor, such that by using a contact pressure conversion model which defines a correlation between the amplitude of the pulse wave signal and the contact pressure, the processor 120 may obtain contact pressure. However, the features are not limited to the aforementioned examples, and may be obtained in various ways.

Figure 2:
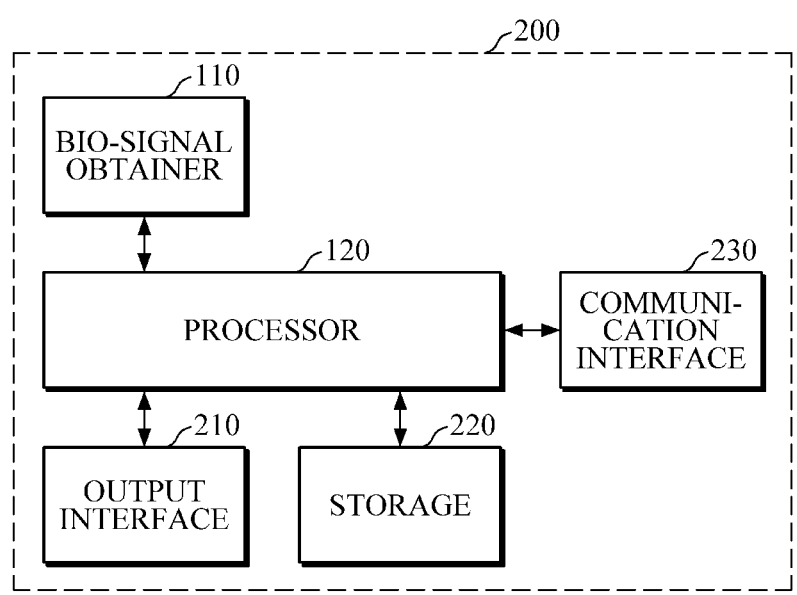
FIG. 2 is a block diagram illustrating an apparatus for estimating bio-information according to another example embodiment.

Referring to FIG. 2, an apparatus 200 for estimating bio-information according to an example embodiment may further include an output interface 210, a storage 220, and a communication interface 230, in addition to the bio-signal obtainer 110 and the processor 120.

In response to a request for estimating bio-information, the bio-signal obtainer 110 may obtain a bio-signal. As described above, the bio-signal obtainer 110 includes a sensor for obtaining the bio-signal, and may obtain the bio-signal using the sensor. Further, the bio-signal obtainer 110 may receive, through the communication interface 230, a bio-signal from an external device for measuring a bio-signal or other device which stores bio-signals.

The processor 120 may obtain an oscillometric waveform envelope from the obtained bio-signal, and may estimate bio-information by using the obtained oscillometric waveform envelope.

The output interface 210 may provide results processed by the processor 120, e.g., an obtained oscillometric waveform envelope graph, an estimated bio-information value, and the like, for a user by using various output modules. The output modules may include a visual output module such as a display and the like, a voice output module such as a speaker and the like, or a haptic module and the like using vibrations, tactile sensation, and the like, but are not limited thereto. For example, the output interface 210 may also output information such as an estimated blood pressure value and/or health condition determined based on the estimated blood pressure value, actions in response to the determined health condition, and the like. Further, the output interface 210 may output a blood pressure estimation history in the form of graphs, and may provide detailed information related to estimating blood pressure at a corresponding time point selected by a user.

The storage 220 may store reference information related to estimating bio-information, a bio-information estimation result, and the like. For example, the reference information may include information, such as user characteristic information including a user's age, sex, health condition, and the like, a bio-information estimation model, and the like.

The storage 220 may include at least one storage medium of a flash memory type memory, a hard disk type memory, a multimedia card micro type memory, a card type memory (e.g., a secure digital (SD) memory, an extreme digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communication interface 230 may communicate with an external device by using communication modules, and may transmit and receive a variety of information to and from the connected external device. Examples of the external device may include a sensor for measuring a bio-signal, a blood pressure measuring device such as a cuff manometer, a medical device related to measuring bio-information, and an information processing device such as a smartphone, a tablet personal computer (PC), a desktop computer, a laptop computer, and the like. For example, the communication interface 230 may receive a bio-signal, cuff pressure, a bio-information estimation model, a contact pressure conversion model, and the like from the external device. Further, the communication interface 230 may transmit information, such as the bio-signal obtained by the bio-signal obtainer 110, the oscillometric waveform envelope obtained by the processor 120, the characteristic point detected for estimating bio-information, the estimated bio-information value, and the like, to the external device.

The communication interface 230 may communicate with an external device by using various wired or wireless communication techniques such as Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WI-FI communication, Radio Frequency Identification (RFID) communication, 3G, 4G, and 5G telecommunications, and the like. However, this is merely exemplary and is not intended to be limiting.

Figure 3A:
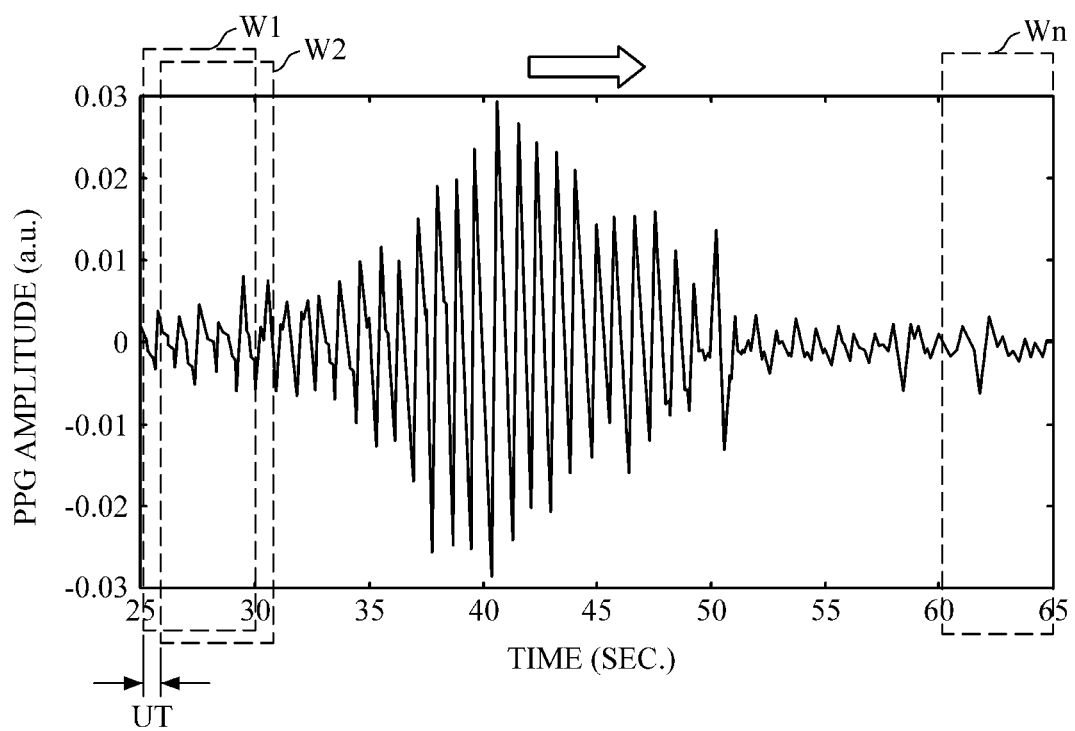
FIGS. 3A, 3B, and 3C are diagrams explaining an example of obtaining an oscillometric waveform envelope.
Figure 3B:
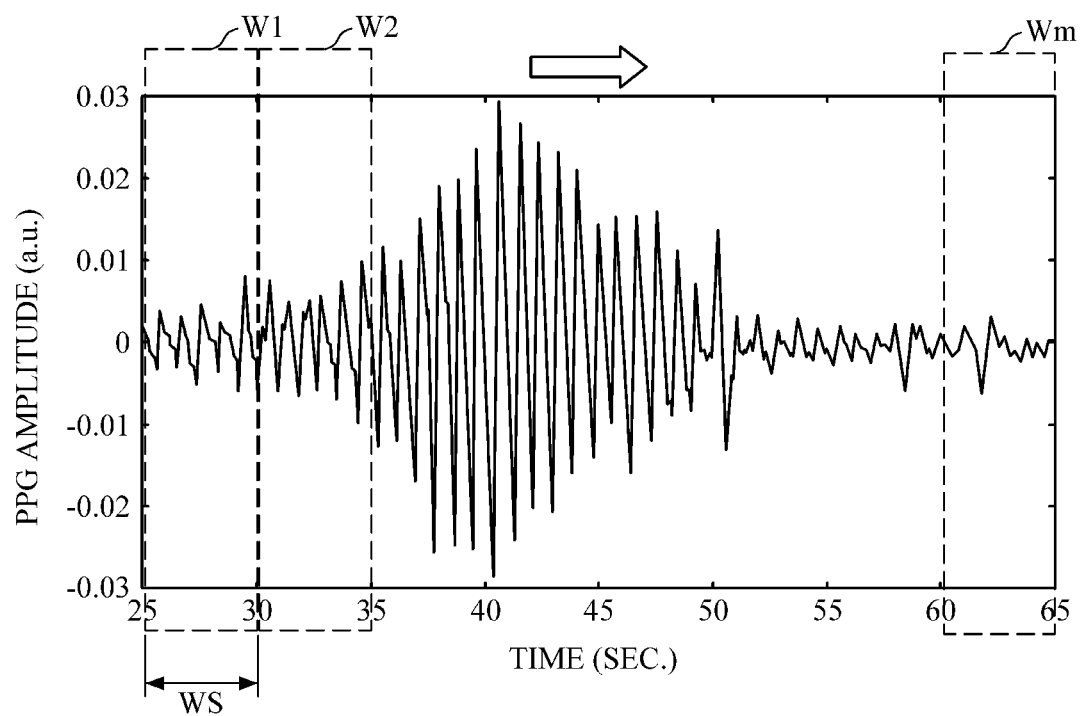
Figure 3C:
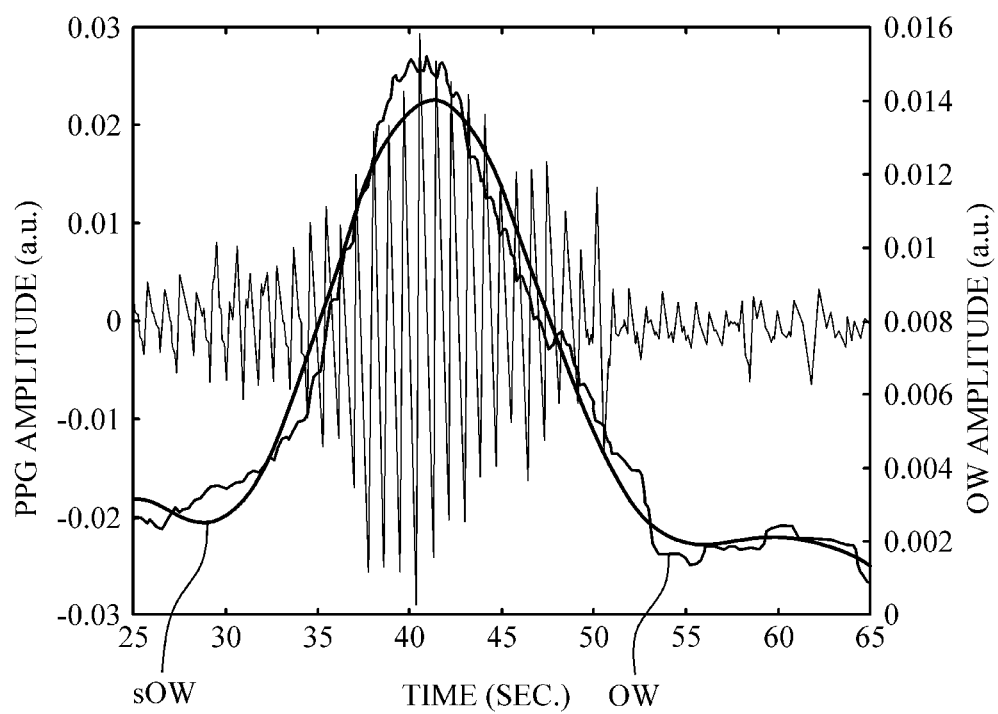

FIGS. 3A to 3C are diagrams explaining an example of obtaining an oscillometric waveform envelope.

Hereinafter, a method of obtaining an oscillometric waveform envelope from a pulse wave signal by the processor 120 of FIGS. 1 and 2 will be described with reference to FIGS. 3A to 3C.

Upon receiving a pulse wave signal from the bio-signal obtainer 110, the processor 120 may obtain a function value by applying a predetermined function to the pulse wave signal, contained in a window, while sliding the window of a predetermined size (e.g., 5 seconds) by a predetermined interval on a time axis of the pulse wave signal. The predetermined window size may be set based on one or more of a user input, a total sampling rate of the pulse wave signal, accuracy required for an estimated bio-information value, a user characteristic (e.g., age, sex, health condition, etc.), an external environment characteristic (e.g., temperature and humidity during measurement, etc.), and a type of bio-information to be estimated, but is not limited thereto.

For example, as illustrated in FIG. 3A, by applying a predetermined function to the pulse wave signal within a window W1 of a first section of the pulse wave signal, the processor 120 may calculate a function value for the window W1 of the first section. Upon calculating the function value for the first section, the processor 120 may shift the window by a reference interval (UT), e.g., by one sampling interval according to a sampling rate of the pulse wave signal, to calculate a function value for a window W2 of a second section, and in this manner, the processor 120 may calculate function values until a window Wn of a last section of the pulse wave signal while sliding the window.

FIG. 3B is a diagram illustrating an example of calculating function values for the windows W1, W2, . . . , and Wm of each section of the pulse wave signal by sliding the window in units of a window size WS. As described above, the time interval for shifting the window may be preset based on a total sampling rate of the pulse wave signal, accuracy required for an estimated bio-information value, a user characteristic, and the like.

For example, the predetermined function, which is applied to the windows of each section, may be a function for converting an alternating current (AC) component of the pulse wave signal into an equivalent direct current (DC) component, and may be, for example, a function for obtaining a root mean square (RMS), as represented by the following Equation 1.

$$fi = \sqrt{\frac{1}{N}(X_1^2 + X_2^2 + \cdots + X_N^2)} \quad \text{[Equation 1]}$$

Herein, fi denotes an RMS value for a window of an i-th section, and N denotes the number of amplitude values of the pulse wave signal, of which an RMS value within the window is to be obtained. For example, N may be a total number of samples corresponding to a size of each window, in which case the number of samples may be calculated based on a sampling rate per second. However, N is not limited thereto, and in consideration of various conditions such as computing performance, required accuracy of bio-information, speed in estimating bio-information, and the like, the number of amplitude values to be calculated may be pre-adjusted by extracting only a portion the samples, among the total number of samples within each window, at a plurality of sampling intervals, and the like. X may be an amplitude value of the pulse wave signal of each sample within the windows.

Referring to FIG. 3C, upon calculating the RMS value for each window, the processor 120 may obtain an oscillometric waveform envelope OW by connecting the calculated function values. In this case, by performing interpolation based on function values of two adjacent sections, the processor 120 may also obtain a function value for a point between the two sections.

Upon obtaining oscillometric waveform envelope OW, the processor 120 may obtain an equalized oscillometric waveform envelope sOW by applying a preprocessing algorithm. In this case, the preprocessing algorithm may include Savitzky-Golay filtering, polynomial fitting, Gaussian fitting, and the like, but is not limited thereto.

In another example, the predetermined function applied to the windows of each section may be, for example, a function for obtaining a sum of absolute values, i.e., sum of absolute (ABS), of amplitude values of each window, as represented by the following Equation 2. In this case, a first ABS value of amplitude values greater than a specific reference amplitude value, e.g., a point having an amplitude value of 0, and a second ABS value of amplitude values lower than the reference amplitude value may be obtained.

$$fi, pos = \sum_{n=1}^{N} |Xn| \ (Xn > 0)$$

$$fi, neg = \sum_{n=1}^{N} |Xn| \ (Xn < 0)$$

[Equation 2]

Herein, fi,pos denotes the first ABS value, i.e., a sum of absolute values of positive (+) amplitude values in the window of the i-th section when the reference amplitude value is '0'; fi,neg denotes the second ABS value, i.e., a sum of absolute values of negative (−) amplitude values in the window of the i-th section when the reference amplitude value is '0'; and N denotes the number of amplitude values to be calculated within the windows, as described above. Further, X denotes amplitude values within the windows.

Upon obtaining the first ABS value and the second ABS value, the processor 120 may obtain the oscillometric waveform envelope OW, as illustrated in FIG. 3C, by combining the first ABS value and the second ABS value. In this case, upon obtaining the first ABS value and the second ABS value, the processor 120 may apply a preprocessing algorithm, such as Savitzky-Golay filtering, polynomial fitting, Gaussian fitting, and the like, to each of the first ABS value and the second ABS value, to equalize the signal, and may obtain the equalized oscillometric waveform envelope sOW by combining the equalized first ABS value and second ABS value. In this case, the first ABS value and the second ABS value may be combined by using, for example, a combination function such as multiplication, addition, and the like, but is not limited thereto.

Figure 4:
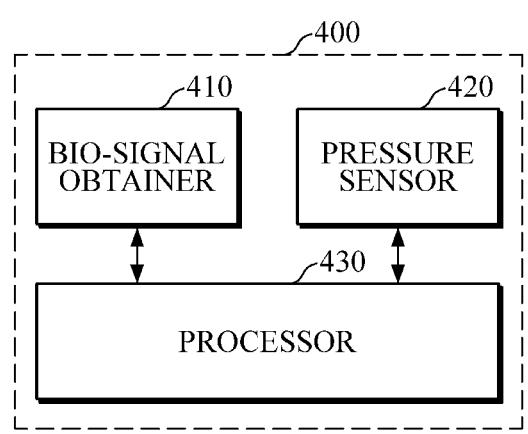
FIG. 4 is a block diagram illustrating an apparatus for estimating bio-information according to yet another example embodiment.
Figure 5:
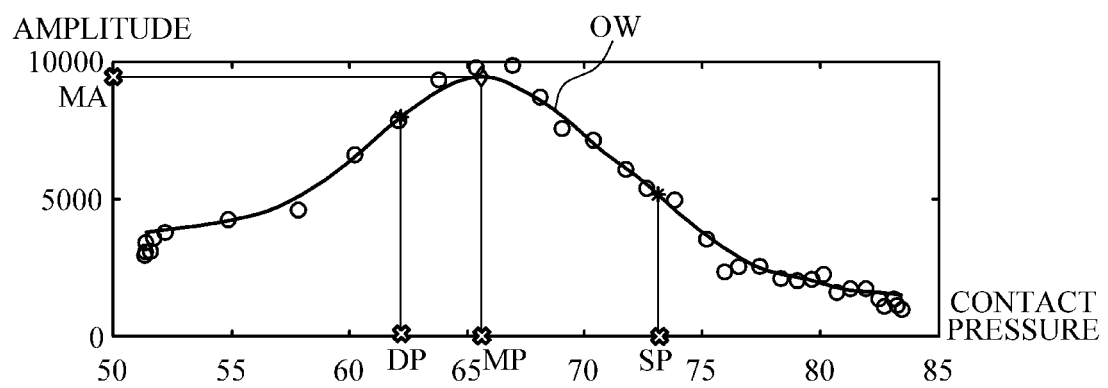
FIG. 5 is a diagram explaining an example of extracting a characteristic point from an oscillometric waveform envelope.

FIG. 4 is a block diagram illustrating an apparatus 400 for estimating bio-information according to yet another example embodiment. FIG. 5 is a diagram explaining an example of extracting a characteristic point from an oscillometric waveform envelope.

Referring to FIG. 4, the apparatus 400 for estimating bio-information includes a bio-signal obtainer 410, a pressure sensor 420, and a processor 430.

The bio-signal obtainer 410 obtains a bio-signal of an object in response to a request for estimating bio-information. The bio-signal obtainer 410 may obtain a bio-signal from a user's object through an internal bio-signal measuring sensor, or may obtain a bio-signal from an external device.

The pressure sensor 420 may measure a change in pressure applied to the object while the bio-signal is measured from the object. For example, the pressure sensor 420 may measure contact pressure when the user touches a pulse wave sensor with the object for measuring a bio-signal and gradually increases or decreases a pressing force applied to the pulse wave sensor.

The processor 430 may estimate bio-information, e.g., blood pressure, by using the pulse wave signal, measured by the pulse wave sensor, and the contact pressure measured by the pressure sensor 420.

The processor 430 may obtain an oscillometric waveform envelope based on a function value of each section of the pulse wave signal while sliding a predetermined window as described above. Further, the processor 430 may detect a maximum peak MA of the oscillometric waveform envelope OW, and may estimate blood pressure based on the detected maximum peak and the contact pressure.

For example, as illustrated in FIG. 5, upon obtaining the oscillometric waveform envelope OW, the processor 430 may obtain a contact pressure versus amplitude value graph by plotting amplitude values of the oscillometric waveform envelope against contact pressure values at each measurement time point. The processor 430 may obtain a contact pressure value MP, corresponding to a maximum amplitude value MA of the oscillometric waveform envelope, and contact pressure values DP and SP, corresponding to amplitude values having a predetermined ratio (e.g., 0.5 to 0.7) to the maximum amplitude value MA, as features for estimating blood pressure.

Upon extracting the features, the processor 430 may estimate bio-information by applying a bio-information estimation model. The bio-information estimation model may be defined as various linear or non-linear combination functions, such as addition, subtraction, division, multiplication, logarithmic value, regression equation, and the like, with no specific limitation. For example, the following Equation 3 represents a simple linear function.

$$y=ax+b \qquad \text{[Equation 3]}$$

Herein, y denotes an estimated bio-information value to be obtained; x denotes an extracted feature value; and a and b are values pre-obtained by preprocessing, and may be defined differently according to the types of bio-information, a user characteristic, etc. For example, the blood pressure estimation model may be defined for each of mean arterial pressure (MAP), diastolic blood pressure (DBP), and systolic blood pressure (SBP), and the processor 430 may independently estimate each blood pressure by using a blood pressure estimation model defined for each of MAP, DBP, and SBP. For example, by inputting the extracted feature values MP, DP, and SP into functions for estimating MAP, DBP, and SBP respectively, the processor 430 may obtain MAP, DBP, and SBP independently.

Figure 6:
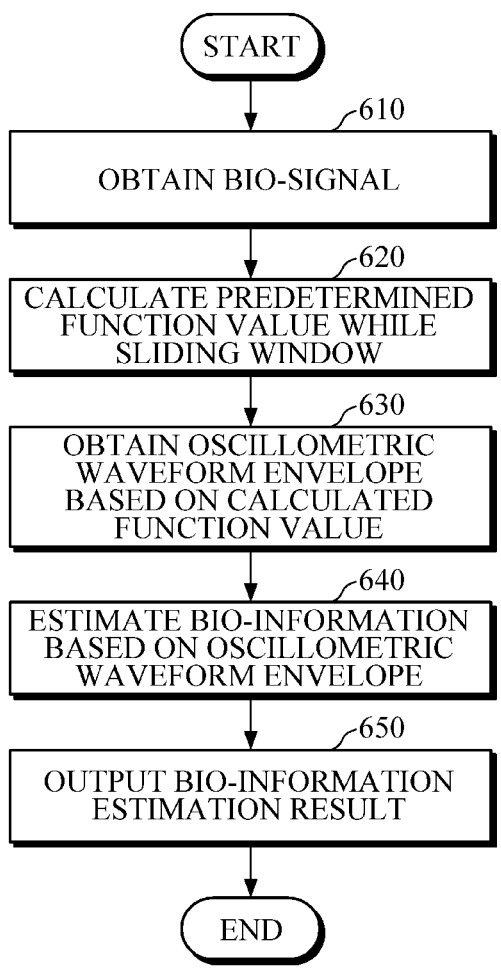
FIG. 6 is a flowchart illustrating a method of estimating bio-information according to an example embodiment.

FIG. 6 is a flowchart illustrating a method of estimating bio-information according to an example embodiment. The method of estimating bio-information of FIG. 6 may be performed by any one of the aforementioned embodiments of the apparatuses 100, 200, and 400 for estimating bio-information, which is described above in detail and thus will be briefly described below.

The apparatuses 100, 200, and 400 for estimating bio-information may obtain a bio-signal of an object in 610. Upon obtaining the bio-signal, the apparatuses 100, 200, and 400 for estimating bio-information may preprocess the bio-signal by using various preprocessing methods, such as band-pass filtering and the like.

The apparatuses 100, 200, and 400 for estimating bio-information may calculate predetermined function values for each window in 620 while sliding the window of a predetermined size by a predetermined interval on a time axis of the bio-signal obtained in 610. In this case, the predetermined function may be a function for obtaining a root mean square (RMS) or a sum of absolute (ABS) of amplitude values of the pulse wave signal contained in each window, and the like.

Figure 7:
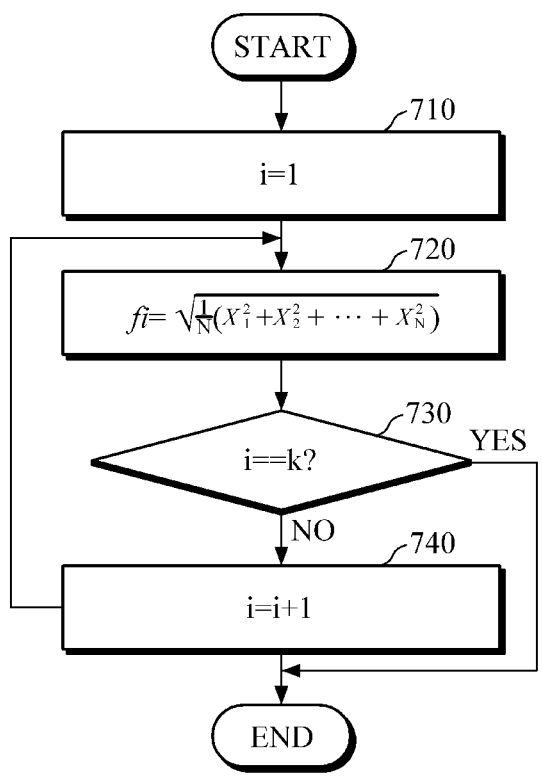
FIGS. 7 and 8 are diagrams illustrating examples of calculating predetermined function values.
Figure 8:
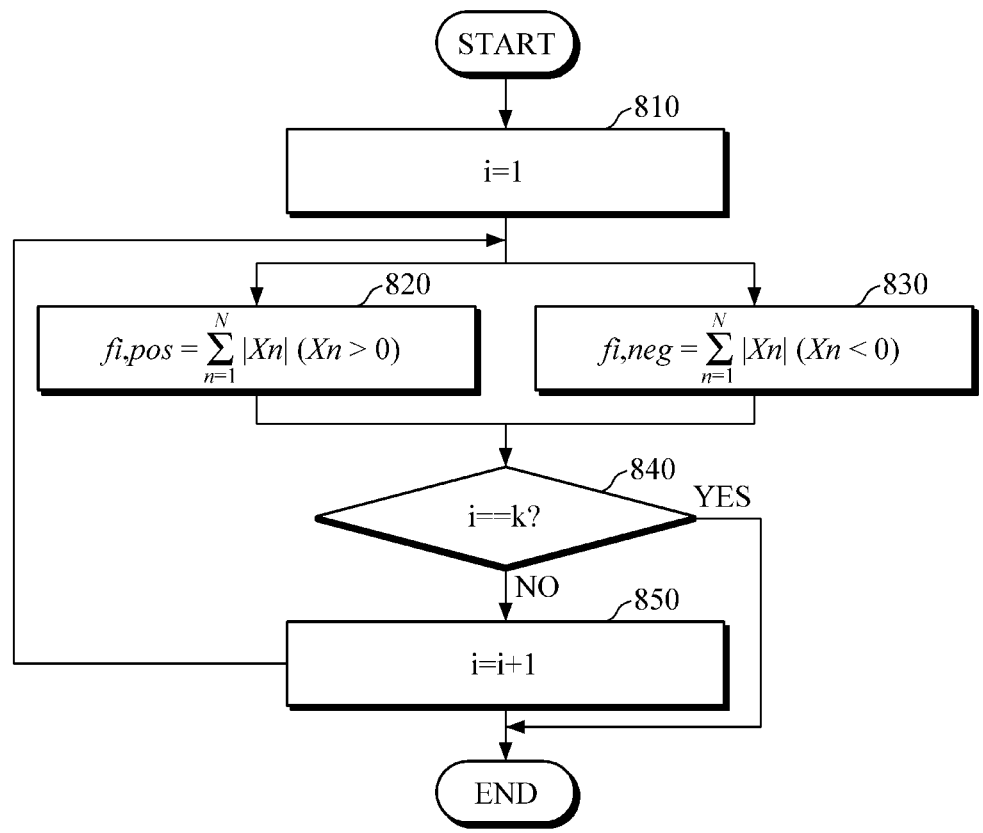

FIGS. 7 and 8 are diagrams illustrating examples of calculating predetermined function values. The examples of calculating a predetermined function value for each window in 620 will be described below with reference to FIGS. 7 and 8.

For example, referring to FIG. 7, when sliding a window, an index i, indicating a current section in which the current window is located, is initialized in 710.

Then, by locating the window in an i-th section of the bio-signal, and calculating the RMS of the amplitude values X contained in the window, an i-th function value fi may be calculated in 720. In this case, the number of amplitude values contained in each window may be the number of samples corresponding to a window size.

Subsequently, upon comparing the index i of the current section with an index k of a last section in 730, if the index i is equal to the index k, the calculation is terminated, and if not, the index i is increased by 1, and then operations 710 and 720 are performed again in 740.

In another example, referring to FIG. 8, when sliding a window, an index i, indicating a current section in which the current window is located, is initialized in 810.

Then, by locating the window in an i-th section of the bio-signal, and calculating the ABS of the amplitude values X contained in the window, an i-th first function value fi,pos may be calculated in 820, and by calculating the ABS of negative amplitude values X contained in the window, an i-th second function value fi,neg may be calculated in 830.

Subsequently, upon comparing the index i of the current section with an index k of the last section in 840, if the index i is equal to the index k, the calculation is terminated; and if not, the index i is increased by 1, and then operations 810 and 820 are performed again in 850.

Referring back to FIG. 6, the apparatuses 100, 200, and 400 for estimating bio-information may obtain an oscillometric waveform envelope based on the function values calculated for each window in 630. For example, the apparatuses 100, 200, and 400 for estimating bio-information may obtain the oscillometric waveform envelope by plotting the function values, obtained for each window of the bio-signal, on a graph with an x-axis representing time and a y-axis representing amplitude, and by connecting the function values. In this case, by performing interpolation based on function values of adjacent sections, a function value for a point between the adjacent sections may be obtained. In addition, the apparatuses 100, 200, and 400 for estimating bio-information may equalize the obtained oscillometric waveform envelope by using a preprocessing algorithm.

Next, the apparatuses 100, 200, and 400 for estimating bio-information may estimate bio-information based on the obtained oscillometric waveform envelope in 640. For example, the apparatuses 100, 200, and 400 for estimating bio-information may extract features, such as a peak of the oscillometric waveform envelope, and may estimate bio-information based on the extracted features. For example, the apparatuses 100, 200, and 400 for estimating bio-information may obtain contact pressure applied by the object to the pulse wave sensor during measurement of the pulse wave signal, and may estimate blood pressure based on the oscillometric waveform envelope and the contact pressure.

Then, the apparatuses 100, 200, and 400 for estimating bio-information may output a bio-information estimation result in 650. The apparatuses 100, 200, and 400 for estimating bio-information may output the bio-information estimation result, a bio-information estimation history, warning information, and the like by visual/non-visual methods using various output modules such as a display module, a speaker module, a haptic module, and the like.

Figure 9:
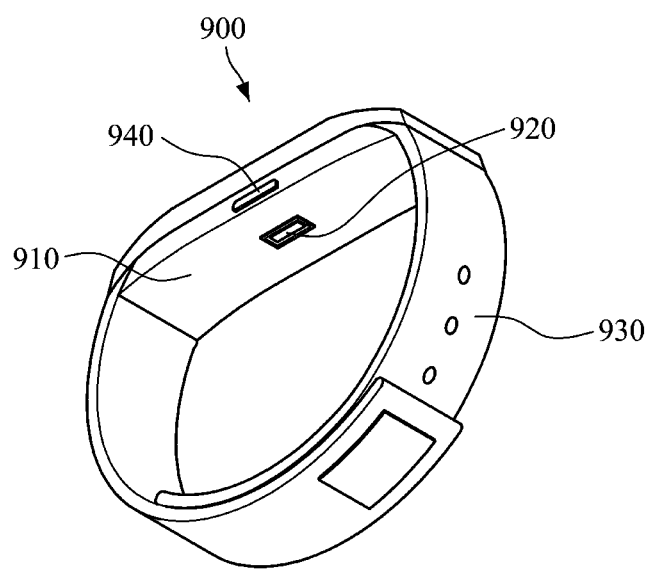
FIG. 9 is a diagram illustrating a wearable device according to an example embodiment.

FIG. 9 is a diagram illustrating an example of a wearable device worn on an object. Any one of the apparatuses 100, 200, and 400 for estimating bio-information according to the aforementioned example embodiments may be mounted in a smart watch worn on a wrist or a smart band-type wearable device, but are not limited thereto.

Referring to FIG. 9, the wearable device 900 includes a main body 910 and a strap 930.

The main body 910 may be formed to have various shapes, and may include various modules which are mounted inside or outside of the main body 910 to perform the aforementioned function of estimating bio-information, as well as various other functions (e.g., time, alarm, etc.). A battery may be embedded in the main body 910 or the strap 930 to supply power to the various modules of the wearable device 900.

The strap 930 may be connected to the main body 910. The strap 930 may be flexible so as to be wrapped around a user's wrist. The strap 930 may be bent in a manner that allows the strap 930 to be detached from the user's wrist or may be formed as a band that is not detachable. Air may be injected into the strap 930 or an airbag may be included in the strap 930, so that the strap 930 may have elasticity according to a change in pressure applied to the wrist, and the change in pressure of the wrist may be transmitted to the main body 910.

The main body 910 may include a sensor 920 for measuring a bio-signal. The sensor 920 may include various sensors, e.g., an optics-based sensor, an impedance-based sensor, a pressure-based sensor, and the like, depending on the types of bio-signals to be obtained. The sensor 920 may be mounted on a surface of the main body 910 which comes into contact with a user's wrist when the main body 910 is worn on the user's wrist. For example, the sensor 920 may include a light source for emitting light onto the wrist and a detector for detecting light scattered or reflected from body tissue such as a skin surface, blood vessels, and the like.

In addition, a processor may be mounted in the main body 910, and may be electrically connected to various modules of the wearable device 900 to control operations thereof.

The processor may control the sensor 920 in response to occurrence of a bio-information estimation event. The bio-information estimation event may be generated in response to a user's command input through a touch screen of a manipulator 940 or a display, at predetermined bio-information estimation intervals, or by monitoring a bio-information estimation result.

Once the bio-signal is measured, the processor may obtain an oscillometric waveform envelope from the bio-signal. For example, while sliding a window of a predetermined size on a time axis of the bio-signal, the processor may obtain function values, such as an RMS or an ABS of amplitude values of the bio-signal contained in each window, and may obtain the oscillometric waveform envelope based on the obtained function values. In this case, the processor may perform preprocessing, such as equalization of the oscillometric waveform envelope and the like.

Upon obtaining the oscillometric waveform envelope, the processor may extract various features, including a peak of the oscillometric waveform envelope. The processor may estimate bio-information, related to cardiovascular status such as blood pressure, by using the extracted features.

In addition, the main body 910 may include a pressure sensor for measuring a change in contact pressure when the object, which is in contact with the sensor 920, changes contact pressure. For example, while wearing the main body 910 on the wrist of one hand, a user nay change contact pressure by pressing a display with a finger of the other hand, and the pressure sensor may measure a change in the contact pressure.

Upon measuring the oscillometric waveform envelope and the contact pressure, the processor may estimate blood pressure based on oscillometry using a peak of the oscillometric waveform envelope, contact pressure values located at time points before and after the peak point and corresponding to amplitude values having a predetermined ratio to the amplitude value of the peak point, and the like.

The display may be mounted on a front surface of the main body 910, and may be a touch panel having a touch screen for sensing a touch input. The display may receive a touch input from a user, may transmit the received touch input to the processor, and may display a processing result of the processor. For example, the display may display a bio-information estimation result, and may display additional information, such as a bio-information estimation history, a change in health condition, warning information, and the like, along with the estimation result.

A storage, which stores processing results of the processor and a variety of information, may be mounted in the main body 910. In this case, the variety of information may include information related to estimating bio-information, as well as information related to other functions of the wearable device 900.

In addition, the main body 910 may include a manipulator 940 which receives a user's instruction and transmits the received instruction to the processor. The manipulator 940 may include a power button to input a command to turn on/off the wearable device 900.

Moreover, a communication interface, which communicates with an external device, may be mounted in the main body 910. The communication interface may transmit a bio-information estimation result to an external device, so as to output the estimation result to the external device, e.g., an output module of a user's mobile terminal, or to store the estimation result in a storage module of the external device. Furthermore, the communication interface may receive information for supporting various other functions of the wearable device and the like from the external device.

Figure 10:
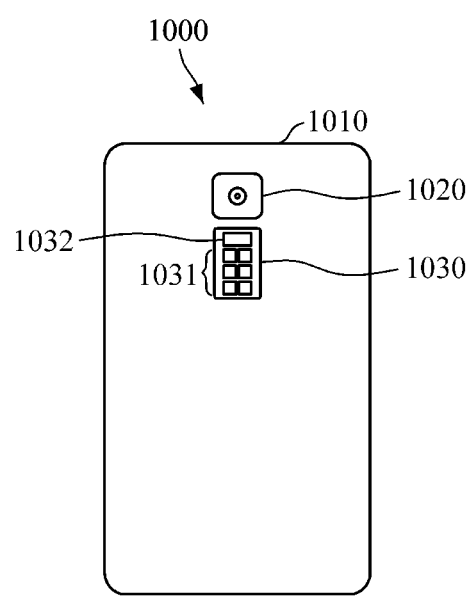
FIG. 10 is a diagram illustrating a smartdevice according to an example embodiment.

FIG. 10 is a diagram illustrating an example of a smart device, to which any one of the apparatuses 100, 200, and 400 for estimating bio-information according to the aforementioned example embodiments are applied. The smart device may include a smartphone and a tablet PC, but is not limited thereto.

Referring to FIG. 10, the smart device 1000 may include a main body 1010, and a sensor 1030 for measuring a bio-signal which is mounted on a surface of the main body 1010. The sensor 1030 may include one or more light sources 1031 and a detector 1032, and may acquire a bio-signal from an object. As illustrated in FIG. 10, the sensor 1030 may be mounted on a rear surface of the main body 1010, but is not limited thereto, and may be configured in combination with a fingerprint sensor or a touch panel mounted on a front surface of the main body 1010.

A display may be mounted on a front surface of the main body 1010. The display may visually display a bio-information estimation result and the like. The display may include a touch panel, and may receive information input through the touch panel and transmit the received information to the processor.

Moreover, an image sensor 1020 may be mounted in the main body 1010. When a user's finger approaches the sensor 1030 to measure a bio-signal, the image sensor 1020 may capture an image of the finger and may transmit the captured image to the processor. Based on the image of the finger, the processor may identify a relative position of the finger with respect to an actual position of the sensor 1030, and may provide the relative position of the finger for the user through the display, so as to guide the user to accurately contact the sensor 1030 with the finger.

The processor may obtain an oscillometric waveform envelope by using the bio-signal measured by the sensor 1030, may estimate bio-information based on the obtained oscillometric waveform envelope, and may output the estimation result through the display.

The example embodiments may be implemented as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments needed for implementing the disclosure may be easily deduced by a person of ordinary skill in the art, to which the disclosure pertains.

According to example embodiments, an apparatus and a method for estimating bio-information are provided, in which bio-information of an object may be estimated with high accuracy by stably obtaining an oscillometric waveform envelope even in a high signal-to-noise environment. Also, according to example embodiments, it is not needed to extract features from the pulse wave signal such as onset and peak locations, and therefore, accuracy in estimating the bio-information may be improved.

Although a few example embodiments have been shown and described, it would be appreciated by those skilled in the art that changes may be made in example embodiments without departing from the principles and spirit of the disclosure, the scope of which is defined in the claims and their equivalents.

What is claimed is:

1. An apparatus for estimating bio-information, the apparatus comprising:
   a sensor configured to obtain a bio-signal from an object; and
   a processor configured to:
   obtain function values by applying a predetermined function to sections of the bio-signal, corresponding to respective windows of a predetermined size, while sliding a window on a time axis of the bio-signal, wherein the predetermined function comprises a function for obtaining a sum of absolute (ABS) value of amplitude values of a section of the bio-signal corresponding to a respective window, the ABS value including a first ABS value of amplitude values greater than a reference amplitude value and a second ABS value of amplitudes values lower than the reference amplitude value, among the amplitude values of the section of the bio-signal;
   apply a preprocessing function to the first ABS value and the second ABS value of each section of the sections of the bio-signal, and obtain an equalized oscillometric waveform envelope by combining the preprocessed first ABS value and the preprocessed second ABS value for each section of the sections of the bio-signal; and
   estimate bio-information of the object based on the equalized oscillometric waveform envelope.

2. The apparatus of claim 1, wherein the bio-signal comprises at least one of photoplethysmogram (PPG), impedance plethysmogram (IPG), pressure wave, and video plethysmogram (VPG).

3. The apparatus of claim 1, wherein the processor is further configured to slide the window by an interval of the predetermined size or by a reference time interval which is smaller than the predetermined size.

4. The apparatus of claim 1, wherein the preprocessing function comprises at least one of Savitzky-Golay filtering, polynomial fitting, and Gaussian fitting.

5. The apparatus of claim 1, wherein the predetermined size is set based on at least one of a user input, a user characteristic, an external environment characteristic, and a type of bio-information to be estimated.

6. The apparatus of claim 1, wherein the processor is further configured to, by applying a combination function including at least one of a multiplication and an addition, combine the first ABS value and the second ABS value.

7. The apparatus of claim 1, wherein the estimated bio-information comprises at least one of blood pressure, vascular age, arterial stiffness, aortic pressure waveform, vascular compliance, stress index, and fatigue level.

8. The apparatus of claim 1, further comprising a pressure sensor configured to obtain a pressure applied by the object while the bio-signal is obtained,
   wherein the processor is further configured to estimate the bio-information based on the equalized oscillometric waveform envelope and the obtained pressure.

9. A method of estimating bio-information, the method comprising:
   obtaining a bio-signal from an object;
   obtaining function values by applying a predetermined function to sections of the bio-signal, corresponding to respective windows of a predetermined size, while sliding a window on a time axis of the bio-signal, wherein the predetermined function comprises a function for obtaining a sum of absolute (ABS) value of amplitude values of a section of the bio-signal corresponding to a respective window, the ABS value including a first ABS value of amplitude values greater than a reference amplitude value and a second ABS value of amplitudes values lower than the reference amplitude value, among the amplitude values of the section of the bio-signal;

applying a preprocessing function to the first ABS value and the second ABS value of each section of the sections of the bio-signal, and obtaining an equalized oscillometric waveform envelope by combining the preprocessed first ABS value and the preprocessed second ABS value for each section of the sections of the bio-signal; and estimating bio-information of the object based on the equalized oscillometric waveform envelope.

10. The method of claim 9, further comprising obtaining a pressure applied by the object while the bio-signal is obtained from the object,
wherein the estimating comprises estimating the bio-information based on the equalized oscillometric waveform envelope and the obtained pressure.

11. The method of claim 9, wherein the preprocessing algorithm comprises at least one of Savitzky-Golay filtering, polynomial fitting, and Gaussian fitting.

* * * * *